United States Patent
Wang (10) Patent No.: US 10,154,506 B2
(45) Date of Patent: Dec. 11, 2018

(54) MBAN CHANNEL MANAGEMENT SCHEME USING PATIENT ACUITY INFORMATION

(71) Applicant: KONINKLIJKE PHILIPS N.V., Eindhoven (NL)

(72) Inventor: Dong Wang, Scarsdale, NY (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 36 days.

(21) Appl. No.: 14/896,795

(22) PCT Filed: Jun. 19, 2014

(86) PCT No.: PCT/IB2014/062408
§ 371 (c)(1),
(2) Date: Dec. 8, 2015

(87) PCT Pub. No.: WO2014/207624
PCT Pub. Date: Dec. 31, 2014

(65) Prior Publication Data
US 2016/0135206 A1    May 12, 2016

Related U.S. Application Data

(60) Provisional application No. 61/840,630, filed on Jun. 28, 2013.

(51) Int. Cl.
*H04W 72/10*    (2009.01)
*H04W 4/70*     (2018.01)
(Continued)

(52) U.S. Cl.
CPC ........... *H04W 72/10* (2013.01); *A61B 5/0024* (2013.01); *H04W 4/70* (2018.02); *H04W 74/006* (2013.01); *H04W 84/18* (2013.01)

(58) Field of Classification Search
CPC ... H04W 4/005; H04W 72/10; H04W 74/006; H04W 84/18; A61B 5/0024
See application file for complete search history.

(56) References Cited

U.S. PATENT DOCUMENTS

2012/0082036 A1* 4/2012 Abedi ................... H04W 84/18
                                                        370/241
2013/0201316 A1* 8/2013 Binder ..................... H04L 67/12
                                                        348/77

FOREIGN PATENT DOCUMENTS

WO     2011/124995     10/2011
WO   WO 2011/124995   * 10/2011  ............ H04W 28/16
(Continued)

OTHER PUBLICATIONS

Delroy Smith: "Philips Healthcare Systems Reply Comments; Amendment of the Commission's Rules to Provide Spectrum for the Operation of Medical Body Area Networks"; Nov. 4, 2009, pp. 1-50, XP055002419.

*Primary Examiner* — Jay Y Lee (57) ABSTRACT manage medical body area network (MBAN) channels to provide differentiated A system (120) and method (150) quality of service (QoS) based on patient acuity level. An available set of channels to be used by a plurality of MBAN systems (52) is identified (154). Channel access rules describing a set of channels for each of a plurality of MBAN priorities are generated (156). The plurality of MBAN priorities are based on patient acuity level. The channel access rules are communicated (158) to the plurality of MBAN systems (52). An MBAN system (52) of the plurality of MBAN systems (52) uses a channel from the set of channels corresponding to an MBAN priority assigned to the MBAN system (52). A hub device (60) configured to use the system (120) and method (150) is also provided.

19 Claims, 4 Drawing Sheets

(51) Int. Cl.
*A61B 5/00* (2006.01)
*H04W 84/18* (2009.01)
*H04W 74/00* (2009.01)

(56) References Cited

FOREIGN PATENT DOCUMENTS

| WO | 2012/120427 | | 9/2012 | | |
|---|---|---|---|---|---|
| WO | WO 2012/120427 | * | 9/2012 | ............ | H04W 72/10 |
| WO | 2012/150534 | | 11/2012 | | |

* cited by examiner

MBAN CHANNEL MANAGEMENT SCHEME USING PATIENT ACUITY INFORMATION

CROSS REFERENCE TO RELATED APPLICATIONS

This application is a national filing of PCT application Ser. No. PCT/IB2014/062408, filed Jun. 19, 2014, published as WO 2014/207624 on Dec. 31, 2014, which claims the benefit of U.S. Provisional Application Number 61/840,630 filed Jun. 28, 2013, which is incorporated herein by reference.

The present application relates generally to wireless communication. It finds particular application in conjunction with medical body area networks (MBANs), and will be described with particular reference thereto. However, it is to be understood that it also finds application in other usage scenarios and is not necessarily limited to the aforementioned application.

There is a general trend in the healthcare industry towards ubiquitous patient monitoring. Ubiquitous patient monitoring provides continuous and patient centric monitoring services during the whole care cycle and can significantly improve quality of care. For example, patient deterioration could be detected at an early stage and early intervention can effectively prevent severe adverse events. MBANs are one of the key enabling technologies for ubiquitous monitoring services. An MBAN replaces the tangle of cables tethering patients to their bedside monitoring units with wireless connections. An MBAN is a low-power wireless network of sensors around and/or on a patient used for monitoring a patient's physiological parameters.

Figure 1:
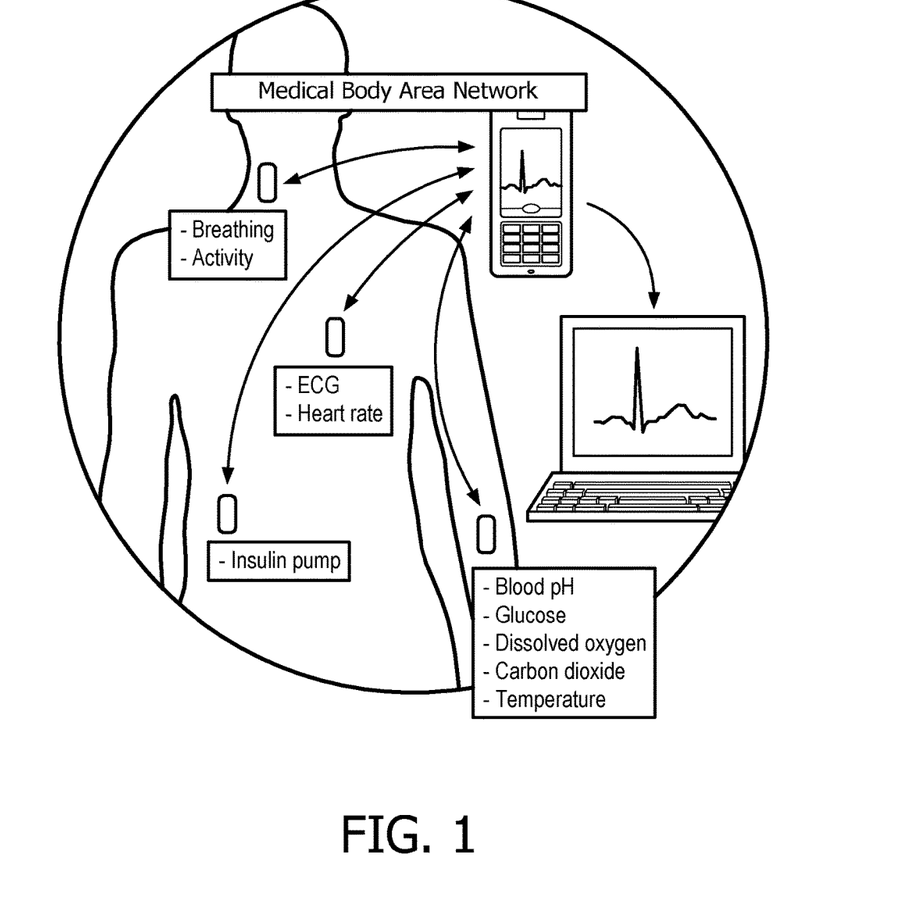
FIG. 1 illustrates a medical body area network (MBAN).

With reference to FIG. 1, a typical MBAN system includes several tiny sensor devices placed around and/or on a patient's body to capture physiological data of the patient, such as heart rate and electriocardiogram (ECG) signals. The captured data is forwarded to a hub device through a short-range and low-power MBAN. The hub device could be a local bedside monitoring device, a cell phone, a set-top-box, or other wireless device and usually has a connection to a backhaul communication network (e.g., a cellular network, such as a 3G or 4G cellular network, a local area network (LAN), etc.). The backhaul communication network is used to transfer the collected data to a remote patient monitoring system. The remote patient monitoring system is responsible for analyzing patients' physiological data and provides one or more of monitoring, diagnosing and treating services in real time.

MBANs provide a low-cost solution to extend patient monitoring services to areas that are currently not monitored (e.g., general wards, patient homes, etc.) and allow patients to walk around without discontinuing monitoring services. This makes it possible to discharge patients earlier from intensive care units (ICUs) or even hospitals, while still providing high quality care monitoring services. This can reduce healthcare costs significantly.

To facilitate MBAN deployment, the U.S. Federal Communications Commission (FCC) has recently allocated a dedicated, MBAN spectrum ranging from 2360 megahertz (MHz) to 2400 MHz for MBAN services. The MBAN spectrum is cleaner than the 2.4 gigahertz (GHz) industrial, scientific and medical (ISM) spectrum, which is currently used by most wireless patient monitoring devices. Further, the MBAN spectrum is useful for meeting medical quality of service (QoS) requirements. However, the MBAN spectrum is still a limited resource and should be used efficiently. Other countries may reserve other spectrum for this use.

Since alarms and measurements of physiological parameters, which could be life critical, are transmitted through MBANs, there is a strict QoS requirement on MBANs, especially for high-acuity patients. Due to increasing MBAN density, as well as patient mobility, multiple MBANs can co-locate with each other. For example, co-location of multiple MBANs is likely to happen in an emergency room (ER) area, where many patients wait for treatment. Since the MBAN channels are usually limited, mutual interference may occur and degrade the QoS of patient monitoring services if MBAN channel accesses are not well coordinated. With the advent of large-scale MBAN deployments, especially in hospitals, there is a growing need to investigate and develop concepts to provide QoS and coexistence of wireless solutions operating side-by-side without mutual adverse effects.

For most known wireless networks that need to share radiofrequency (RF) spectrum (or wireless channels) with other networks, frequency agility solutions have been introduced to avoid and/or mitigate the co-existence interference. For example, in the Institute of Electrical and Electronics Engineers (IEEE) 802.15.4 standard, the clear channel assessment (CCA) mechanism is adopted to help the 802.15.4 coordinator select its operating channel and avoid possible interference from other 802.15.4 networks or other wireless networks working in the 2.4 GHz ISM band.

A challenge with the CCA based channel selection mechanism is that it doesn't provide prioritized MBAN QoS support. All the MBANs are treated as equally important. Therefore, when multiple MBANs compete for a channel, they have equal probability to gain channel access. This may be good for consumer applications, but is undesirable for medical applications since different MBANs may have different importance. For example, an MBAN used for a fitness monitoring application should have much lower importance than an MBAN used for monitoring a high-acuity ICU patient. It is desired that MBANs for high-acuity patients have better access to MBAN channels and thus better QoS support. Conventional distributed frequency agility schemes do not differentiate MBAN QoS requirements of patient monitoring services, which is important for healthcare applications. The QoS requirements of MBANs can be thought of as equivalent to the acuity levels of corresponding patients. In view of the foregoing, an MBAN channel management scheme that can provide differentiated QoS support to different acuity level MBANs is needed.

Moreover, since MBANs can be used to provide monitoring services during the whole care circle of a patient, the acuity level of a patient can change from time to time. In view of this, it is preferable to automatically adjust MBAN priority according to patient acuity level changes without user intervention. End users (e.g., patients, nurses, etc.) usually don't have the expertise to adjust MBAN priority and such intervention can significantly reduce workflow efficiency.

Even more, the distribution of patients' acuity levels can vary greatly at different areas in a medical institution. For example, in a general ward, most monitored patients may have moderate or low acuity, whereas most monitored patients may have high-acuity in an ICU area. An MBAN channel management scheme should consider such variance and provide flexibility to accommodate it.

The present application provides a new and improved system and method which overcome the above-referenced problems and others.

In accordance with one aspect, a medical body area network (MBAN) channel management system is provided.

The MBAN channel management system includes at least one controller configured to identify an available set of channels to be used by a plurality of MBAN systems and to generate channel access rules describing a set of channels for each of a plurality of MBAN priorities. The channels of the set of channels are channels of the available set of channels. The plurality of MBAN priorities correspond to MBAN priorities assigned to the plurality of MBAN systems. The MBAN priorities assigned to the plurality of MBAN systems are based on patient acuity level. The at least one controller is further configured to communicate the channel access rules to the plurality of MBAN systems. An MBAN system of the plurality of MBAN systems uses a channel from the set of channels corresponding to the MBAN priority assigned to the MBAN system.

In accordance with another aspect, a medical body area network (MBAN) channel management method is provided. An available set of channels to be used by a plurality of MBAN systems are identified. Channel access rules describing a set of channels for each of a plurality of MBAN priorities are generated. The channels of the set of channels are channels of the available set of channels. The plurality of MBAN priorities correspond to MBAN priorities assigned to the plurality of MBAN systems. The MBAN priorities assigned to the plurality of MBAN systems are based on patient acuity level. The channel access rules are communicated to the plurality of MBAN systems. An MBAN system of the plurality of MBAN systems uses a channel from the set of channels corresponding to the MBAN priority assigned to the MBAN system.

In accordance with another aspect, a hub device of a medical body area network (MBAN) system is provided. The hub device includes at least one controller configured to determine an MBAN priority based on a patient acuity level of a corresponding patient and receive MBAN channel access rules describing a set of channels for each of a plurality of MBAN priorities. The channels of the set of channels are channels of an available set of channels for a medical institution within which the hub device is used. The plurality of MBAN priorities include the MBAN priority and correspond to MBAN priorities assigned to a plurality of MBAN systems of the medical institution. The at least one controller is further configured to select a channel from the set of channels corresponding to the MBAN priority and to configure an MBAN of the MBAN system to use the selected channel.

One advantage resides in improved patient monitoring.

Another advantage resides in a medical body area network (MBAN) channel management scheme that can provide differentiated quality of service (QoS) support to MBANs with different acuity levels.

Another advantage resides in automatically adjusting MBAN priority according to patient acuity changes without user intervention.

Another advantage resides in accommodating variances in the distributions of acuity levels across different service areas.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

The present application proposes a medical body area network (MBAN) channel management scheme to provide prioritized quality of service (QoS) support to MBANs based on patient acuity level while maintaining MBAN spectrum usage efficiency. In that regard, the MBAN channel management scheme regulates MBAN channel access so that MBANs for higher acuity patients have better access to MBAN channels than lower acuity patients and thus improved QoS support.

Each MBAN has an MBAN priority assigned based on patient acuity level. The MBAN priority can be dynamically updated by a clinical decision support (CDS) engine (e.g., implementing an early warning scoring (EWS) system), which can continuously evaluate and/or predict patient health status. MBAN channel access rules define which MBAN channels can be accessed by MBANs for each MBAN priority. The higher an MBAN priority of an MBAN, the more MBAN channels the MBAN can access. The MBAN channel access rules are distributed to each MBAN hub device to guide its operating channel selection. Such MBAN channel access rules can be tailored specifically for each service area of backhaul access points or for each service zone (e.g., a collection of service areas serving a common division of the medical institution 50, such as intensive care unit (ICU)). Moreover, the channel access rules can be dynamically optimized based on a real-time MBAN priority distribution in each service zone or each service area of backhaul access points.

The MBAN channel management scheme can be used for MBAN based patient monitoring systems. Further, the MBAN channel management scheme can be used with the MBAN spectrum (i.e., 2360 megahertz (MHz) to 2400 MHz), the 2.4 gigahertz (GHz) industrial, scientific and medical (ISM) spectrum, or any other radiofrequency (RF) spectrum used by MBAN based patient monitoring systems.

Figure 2:
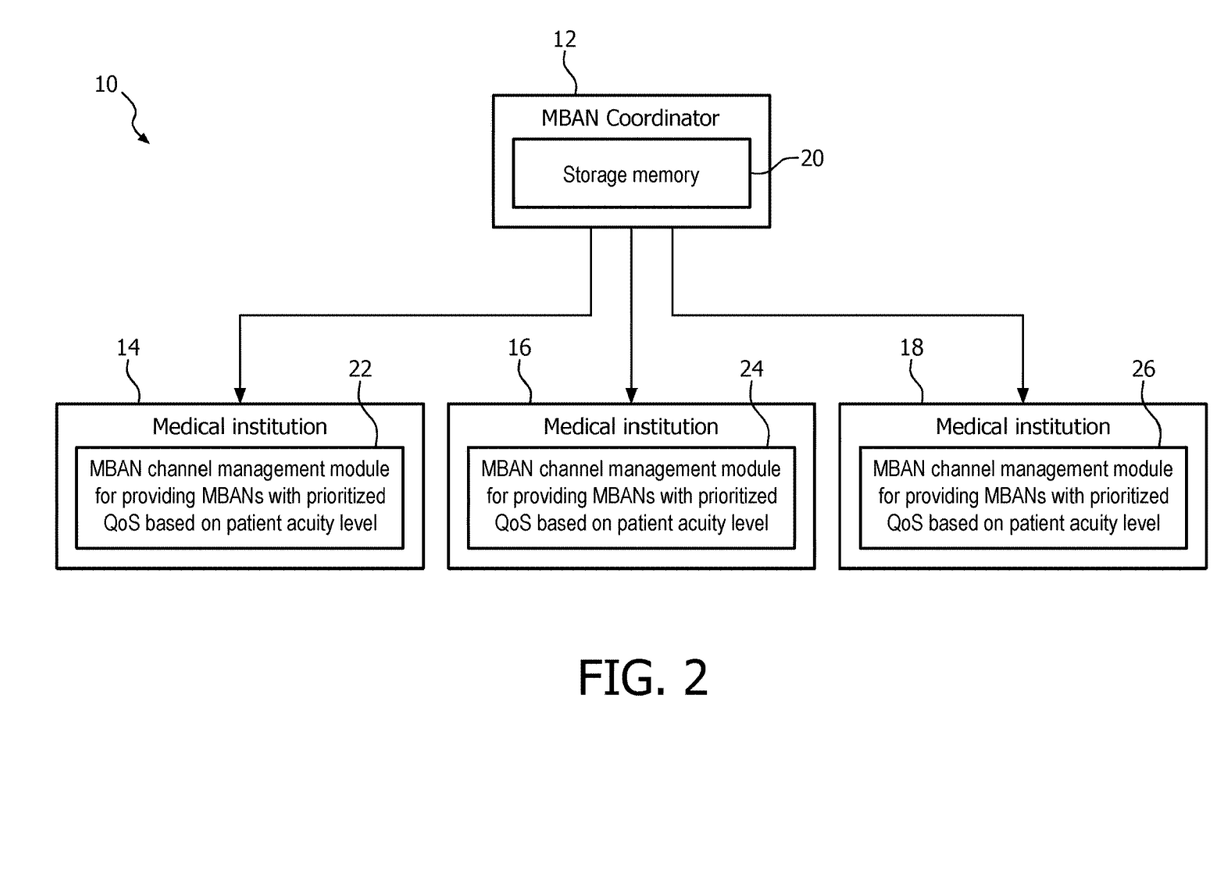
FIG. 2 illustrates an MBAN coordinator managing the use of a spectrum across one or more medical institutions equipped with an enhanced MBAN channel management scheme.

With reference to FIG. 2, a system 10 includes a medical body area network (MBAN) coordinator 12. The MBAN coordinator 12 coordinates the use of at least a portion of a managed spectrum, typically the MBAN spectrum, by one or more medical institutions 14, 16, 18 registered with the MBAN coordinator 12. Typically, the managed spectrum is authorized by a governmental agency, such as the Federal Communications Commission (FCC) in the U.S., for use by the registered medical institutions 14, 16, 18. The MBAN coordinator 12 coordinates the use of the managed spectrum according to one or more coordination rules determined by the authorizing party, typically to avoid interference issues.

Through application of the rules, the MBAN coordinator 12 selectively authorizes the registered medical institutions 14, 16, 18 to use the managed spectrum by providing control messages to the registered medical institutions 14, 16, 18. The control messages for a registered medical institution 14, 16, 18 includes data about the frequencies of the managed spectrum the registered medical institution 14, 16, 18 is authorized to use, optionally with time restrictions (e.g., time periods for MBAN operations, effective time and/or date, and expiration time and/or date) and/or a unique identifier (ID) for the registered medical institution. The control messages can be provided to the registered medical institutions 14, 16, 18 in any manner suitable for transporting data, such as automatically through a network or manually using email or the like.

At least one storage memory 20 of the MBAN coordinator 12 maintains data on current authorizations to facilitate coordination. For example, the MBAN coordinator 12 can track current authorizations to better coordinate the sharing of the managed spectrum with other users. Further, in some embodiments, the MBAN coordinator 12 maintains registration records for each of the registered medical institutions 14, 16, 18 in the storage memory 20. Each of the registration records suitably includes a unique ID for the corresponding registered medical institution 14, 16, 18 and optionally data regarding control messages provided to the registered medical institution 14, 16, 18 and/or data required for registration, such as name, address, phone number, etc.

Each of the registered medical institutions 14, 16, 18 includes an MBAN channel management module 22, 24, 26. The MBAN channel management module 22, 24, 26 for a registered medical institution 14, 16, 18 receives data describing the frequencies authorized for use by the registered medical institution 14, 16, 18 from the MBAN coordinator 12, directly or indirectly, by way of control messages. Based on the authorized frequencies, the MBAN channel management module 22, 24, 26 distributes MBAN channel access rules to MBANs of the corresponding registered medical institution 14, 16, 18. MBAN channel access rules indicate which MBAN channels of the authorized frequencies can be used for each MBAN priority, where MBAN priority is based on patient acuity level. The MBANs then use the MBAN channels associated with corresponding patient acuity levels of the MBANs. The MBAN channel management module 14, 16, 18 is typically software stored on a memory and executed by a processor.

Figure 3:
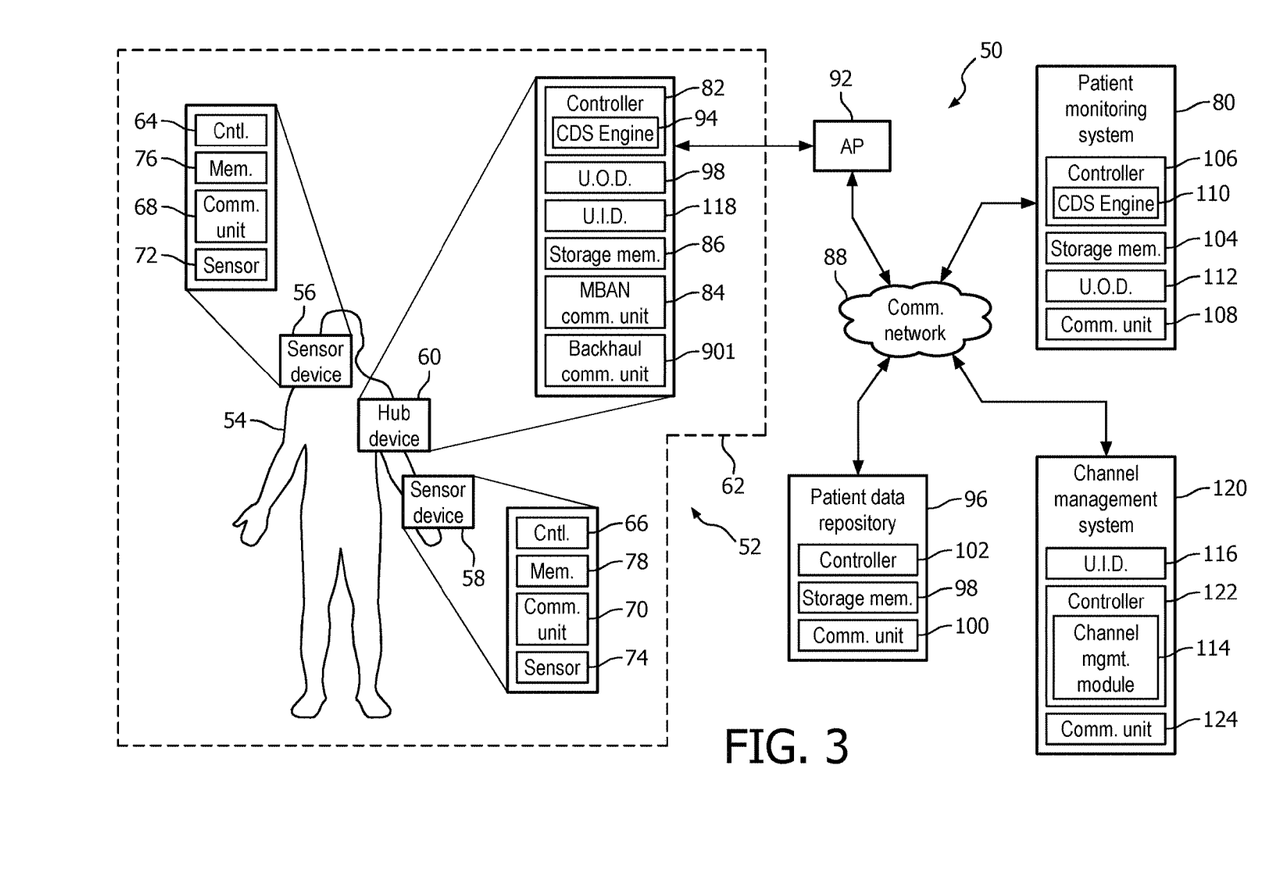
FIG. 3 illustrates a medical institution equipped with an enhanced MBAN channel management scheme.

With reference to FIG. 3, a medical institution 50, such as one of the registered medical institutions 14, 16, 18, includes one or more MBAN systems 52. The MBAN systems 52 are each associated with a patient 54 and are each deployed to capture physiological data of the patient 54. Further, each of the MBAN systems 52 includes one or more sensor devices 56, 58 and a hub device 60 communicating over an MBAN 62 of the MBAN system 52. The MBAN 62 is a low-power, short-range wireless network. The MBAN 62 can be of any type, such as an Institute of Electrical and Electronics Engineers (IEEE) 802.15.6 MBAN or an IEEE 802.15.4j MBAN.

The sensor devices 56, 68 capture physiological data of the patient 54, such as heart rate, respiration rate, blood pressure, ECG signals, and so forth, in real-time and forward the data to the hub device 60 over the MBAN 62. The sensor devices 56, 58 are typically disposed on the exterior of the patient 54. For example, the sensor devices 56, 58 can be on-body and/or wearable sensor devices. However, in some embodiments, the sensor devices 56, 58 are additionally or alternatively disposed in the patient 54 and/or proximate to the patient 54.

Each of the sensor devices 56, 58 includes a controller 64, 66, a communication unit 68, 70, and at least one sensor 72, 74 for measuring at least one physiological parameter of the patient 54. The controller 64, 66 captures the physiological data using the sensor 72, 74 and transmits the captured physiological data to the hub device 60 using the communication unit 68, 70. The controller 64, 66 can immediately transmit the captured physiological data upon receiving it. Alternatively, the controller 64, 66 can buffer or otherwise store the captured physiological data in a storage memory 76, 78 of the sensor device 56, 58 and only transmit the buffered physiological data when the amount exceeds a threshold. The communication unit 68, 70 communicates with the hub device 60 over the MBAN 62.

Typically, the captured physiological data is transmitted directly to the hub device 60 using the communication unit 68, 70. However, the captured physiological data can be indirectly transmitted to the hub device 60. For example, the sensor devices 56, 58 can transmit the physiological data to a patient-carried unit with, for example, body coupled communications. The patient-carried unit can then transmit the physiological data from all of the sensor devices 56, 58 to the hub device 60.

The hub device 60 one or more of: 1) collects physiological data from the sensor devices 56, 58; 2) manages the sensor devices 56, 58 (e.g., acts as a personal area network (PAN) coordinator); 3) processes collected physiological data locally, typically in real-time; and 4) transfers collected physiological data to a patient monitoring system 80 of the medical institution 50. The hub device 60 is typically disposed proximate to the patient 54. Further, the hub device 60 is typically one of a local bedside monitoring unit, a cell phone, a set-top-box, or other wireless device.

A controller 82 of the hub device 60 can be configured to control an MBAN communication unit 84 of the hub device 60 to set up the MBAN 62, associate/disassociate the sensor device 56, 58 and other devices with the MBAN 62, and so on. The controller 82 can also be configured to collect the captured physiological data from the sensor devices 56, 58 using the MBAN communication unit 84. The MBAN communication unit 84 communicates with the sensor devices 56, 58 using the MBAN 62 and provides the controller 82 with an interface to the MBAN 62.

Physiological data collected by the controller 82 can be transferred to the patient monitoring system 80 by the controller 82. The controller 82 can immediately transfer the collected physiological data to the patient monitoring system 80 upon receiving it. Alternatively, the controller 82 can buffer or otherwise store the collected physiological data in a storage memory 86 of the hub device 60 and only transfer the buffered physiological data when the amount exceeds a threshold.

The controller 82 transfers the collected physiological data to the patient monitoring system 80 over a backhaul communication network 88, such as a wired Ethernet, Wi-Fi, or 3G/4G cellular network, using a backhaul communication unit 90. The backhaul communication network 88 is typically long-range compared to the MBAN 62. When the backhaul communication network 88 includes a wireless interface, it includes one or more backhaul access points 92 for wireless communication. The backhaul communication unit 90 communicates with the patient monitoring system 80 using the backhaul communication network 88 and provides the controller 82 with an interface to the backhaul communication network 88.

Physiological data collected by the controller 82 can also be processed locally by the controller 82 using a clinic decision support (CDS) engine 94. The CDS engine 94 is typically software executed by a processor of the controller 82. The CDS engine 94 provides a patient-centric personalized monitoring service based on the collected physiological data. The CDS engine 94 can also provide the patient-centric personalized monitoring service based on other patient related medical data (e.g., an electronic medical record (EMR), a lab report, etc.) available in one or more patient data repositories 96 of the backhaul communication network 88. The CDS engine 94 typically uses patient data (i.e., the collected physiological data and/or the other patient related medical data) to evaluate and predict patient condition and generate intelligent alarms as necessary.

In response to detecting an alarm condition, the CDS engine 94 can generate warning messages, such as audio and/or visual warning messages using, for example, a user output device 98 (e.g., a display device) of the hub device 60. Additionally, or alternatively, the CDS engine 94 can transmit an alarm message to a remote system or device, such as the patient monitoring system 80, using the MBAN or backhaul communication unit 84, 90 so as to allow the remote system or device to process the alarm and/or alert clinicians.

The patient data repositories 96 store patient medical patient data for the patients 54 of the medical institution 50 in one or more storage memories 98 of the patient data repositories 96. Such patient data may include EMRs, medical history data, lab reports, physiological data, and other relevant patient data. The patient data repository 96 may also store in the storage memories 98 other medical data that may be useful for the clinical decision support algorithms of CDS engines, such as the CDS engine 94. Such other medical data may include medical knowledge, demographic and/or geographic medical data, and so on.

Each of the patient data repositories 96 includes a communication unit 100 and a controller 102. The communication unit 100 allows the controller 102 to communicate with the backhaul communication network 88, and the controller 102 makes the data in the storage memories 98 available to external devices and/or systems over the backhaul communication network 88.

The patient monitoring system 80 one or more of: 1) receives physiological data transferred thereto by the hub devices 60 of the MBAN systems 52 over the backhaul communication network 88; 2) analyzes the received physiological data; 3) stores the received physiological data in a storage memory 104 of the patient monitoring system 80 or in an external system; and 4) provides one or more of monitoring, diagnosing and treating services in real time based on the received physiological data. The patient monitoring system 80 suitably has access to the patient data repositories 96 to facilitate performance of the foregoing tasks. Further, the patient monitoring system 80 is remote from the MBAN systems 52 and typically central to the MBAN systems 52.

A controller 106 of the patient monitoring system 80 can be configured to control a communication unit 108 of the patient monitoring system 80 to receive physiological data from the MBAN systems 52. The communication unit 108 communicates with the backhaul communication network 88 and provides the controller 106 with an interface to the backhaul communication network 88. The received physiological data is suitably stored in the storage memory 104 of the patient monitoring system 80.

Physiological data received by the controller 106 can also be processed locally by the controller 106 using a CDS engine 110. The CDS engine 110 is typically software executed by a processor of the controller 106. The CDS engine 110 provides a patient-centric personalized monitoring service based on the collected physiological data. The CDS engine 110 can also provide the patient-centric personalized monitoring service based on other patient related medical data (e.g., an EMR, a lab report, etc.) available in the patient data repositories. The CDS engine 110 typically uses patient data (i.e., the collected physiological data and/or the other patient related medical data) to evaluate and predict patient condition, and generate intelligent alarms as necessary, for all or a subset of patients for which physiological data is received.

In response to detecting an alarm condition, the CDS engine 110 can generate warning messages, such as audio and/or visual warning messages using, for example, a user output device 112 (e.g., a display device) of the patient monitoring system 80. Additionally, or alternatively, the CDS engine 110 can transmit an alarm message to a remote system or device using the communication unit 108 so as to allow the remote system or device to process the alarm and/or alert clinicians.

For simplicity, only a single patient monitoring system was described. However, it is contemplated that multiple patient monitoring systems are employed. In such instances, the MBAN systems 52 of the medical institution 50 can be assigned to the available patient monitoring systems using any scheme designed to distribute the MBAN systems 52 across the patient monitoring systems. For example, each of the patient monitoring systems can be assigned a service zone of the medical institution 50, and each of the MBAN systems 52 can be assigned to the patient monitoring system corresponding to the service zone within which the MBAN system 52.

An MBAN channel management module 114 receives data describing frequencies available to the medical institution 50 from, for example, a user input device 116 or an external system. For example, where the MBAN spectrum is employed (i.e., the 2360-2400 MHz spectrum), the MBAN channel management module 114 can receive control messages from the MBAN coordinator 12 (FIG. 2) that define the frequencies in the MBAN spectrum that are authorized for MBAN operation. Based on the received data, the MBAN channel management module 114 identifies a set of MBAN channels that are located within the available frequencies for each type of MBAN (e.g., IEEE 802.15.4j or IEEE 802.15.6). Using the identified channels, the MBAN channel management module 114 implements an MBAN channel management scheme to provide prioritized QoS support to the MBAN systems 52 based on patient acuity level while maintaining usage efficiency of the spectrum used by the MBAN systems 52.

To implement the MBAN channel management scheme, the MBAN channel management module 114 defines MBAN channel access rules to regulate the use of the MBAN channels available to the medical institution 50. Through the backhaul communication network 88, the MBAN channel management module 114 forwards the defined channel access rules to the hub devices 60 of the MBAN systems 52 to assist the hub devices 60 in selecting their operating channels. The MBAN channel access rules can be distributed directly to the hub devices 60 or indirectly to the hub devices 60, for example, by way of the access points 92 of the backhaul communication network 88.

The MBAN channel access rules define an MBAN channel set that can be accessed by MBANs for each of a plurality of MBAN priorities. In that regard, each of the MBANs 62 of the medical institution 50 is assigned one of the MBAN priorities based on the acuity level (i.e., life criticality) of the corresponding patient 54. Multiple MBAN priorities can be defined based on the patient acuity levels of the patients 54 of the medical institution 50. The lower the patient acuity level, the lower the MBAN priority. For example, the highest MBAN priority can be assigned to an MBAN of an ICU patient who has the highest acuity level because the data transmitted on this MBAN is most important. Continuing with this example, the lowest MBAN priority can be assigned to an MBAN of a recovered patient whose health status is stable, and other MBAN priorities are in between the highest and lowest MBAN priorities depending on patient acuity level.

The channel set for higher MBAN priorities include more channels than lower MBAN priorities. Typically, the channel set for an MBAN priority i is a subset of the channel set for an MBAN priority j when j>i. In other words, an MBAN with an MBAN priority of j can access all the channels that an MBAN with an MBAN priority of i can access and some other channels that an MBAN with an MBAN priority of i has no right to access. This provides an MBAN with a higher priority more chances to gain MBAN channel access and obtain better QoS.

When an MBAN 62 of the medical institution 50 is initiated, the corresponding hub device 60 can set an MBAN priority in accordance with a priority (or patient acuity level) received from a healthcare professional by a corresponding user input device 118 or in accordance with a patient status evaluation and/or prediction output determined by a CDS engine 94, 110 local to, or remote from, the MBAN 62. Also during its operation, the priority of the MBAN 62 can be updated automatically based on the patient status evaluation and/or prediction output of the CDS engine 94, 110.

As noted above, the MBAN priority of an MBAN 62 of the medical institution 50 can be automatically updated during the whole care cycle. Specifically, a CDS engine 94, 110 can be activated to track and/or predict patient acuity level based on real-time monitoring data and other patient data (e.g., EMR, lab report, etc.). The CDS engine 94, 110 for the MBAN 62 can be local to the MBAN 62 (e.g., implemented by the corresponding hub device 60) or remote from the MBAN 62 (e.g., implemented by the patient monitoring system 80). The CDS engine 94, 110 continuously generates a patient acuity score based on patient health status and maps the score to an MBAN priority level for the MBAN 62. When the MBAN priority level of the MBAN 62 changes, or the MBAN channel access rules of for the MBAN priority level change, the hub device 60 of the MBAN 62 updates its candidate channel set (i.e., its internal set of channels that can be used for MBAN operations).

The MBAN channel access rules can be customized for each service area of the access points 92. A service area is an area served by an access point. The MBAN channel management module 114 can optimize the channel access rules for each service area based on a-prior knowledge about the distribution of acuity levels of patients in the service area. For example, more MBAN channels can be reserved for high priority MBANs for an access point serving an ICU area in which most of monitored patients are with high acuity levels. Continuing with this example, less MBAN channels can be reserved for high priority MBANs for an access point serving a general ward area in which most of monitored patients are with moderate or low acuity levels. Low, medium and high acuity levels are defined by dividing the range of acuity levels into thirds, where acuity levels falling in the lowest range (i.e., third) are deemed as low, acuity levels falling in the highest range (i.e., third) are deemed as high, and acuity levels falling in the middle range (i.e., third) are deemed medium. More generally, the foregoing example can be described as increasing the number of channels for the most prominent MBAN priorities, where the most prominent MBAN priorities are those MBAN priorities most prominent in the MBAN priority distributions. The foregoing optimization will allow the MBAN channels to be efficiently used while avoiding possible interference to high priority MBANs.

The MBAN channel access rules can also be customized for each service zone (i.e., a collection of service areas) of the medical institution 50. In that regard, the MBAN channel management module 114 can divide the medical institution 50 into multiple service zones based on the a-prior knowledge about the distribution of the acuity levels of patients in the service areas of the access points 92. For each service zone, the MBAN channel management module 114 can optimize the channel access rules to enhance spectral use efficiency while minimizing possible interference to high priority MBANs. The immediately preceding example regarding service areas can be applied to service zones in the same way as done for service areas.

The MBAN channel access rules can be dynamically optimized to adapt to real-time MBAN distributions of acuity levels. Due to patient mobility, the distribution of MBAN priorities in a service zone or a service area can change from time to time. Since the hub devices 60 of the medical institution 50 are typically connected to the MBAN channel management module 114 by way of the access points 92, the MBAN channel management module 114 can obtain the MBAN priority distribution, or a reasonable approximation thereof, in the serving area of each individual access point. Therefore, the MBAN channel management module 114 can optimize the channel access rules for each individual access point or service zone continuously based on the real-time data about the MBAN priority distribution of the service area of the access points 88. For example, the MBAN priority distribution in an emergency room area could vary in a wide range from time to time, whereby the continuous optimization of the channel access rules would be useful to improve the MBAN spectral usage efficiency.

The MBAN channel management module 114 can be implemented in software and/or hardware to carry out the above described functionality. However, the MBAN channel management module 114 is suitably software implemented by a server connected to the backhaul communication network 88, such as a channel management system 120 or the patient monitoring system 80. As illustrated, the channel management system 120 includes a controller 122 and a communication unit 124. The controller 122 executes processor executable instructions describing the MBAN channel management module 114 using a processor of the controller 122. The communication unit 124 provides the controller 122 with an interface to the backhaul communication network 88.

Figure 4:
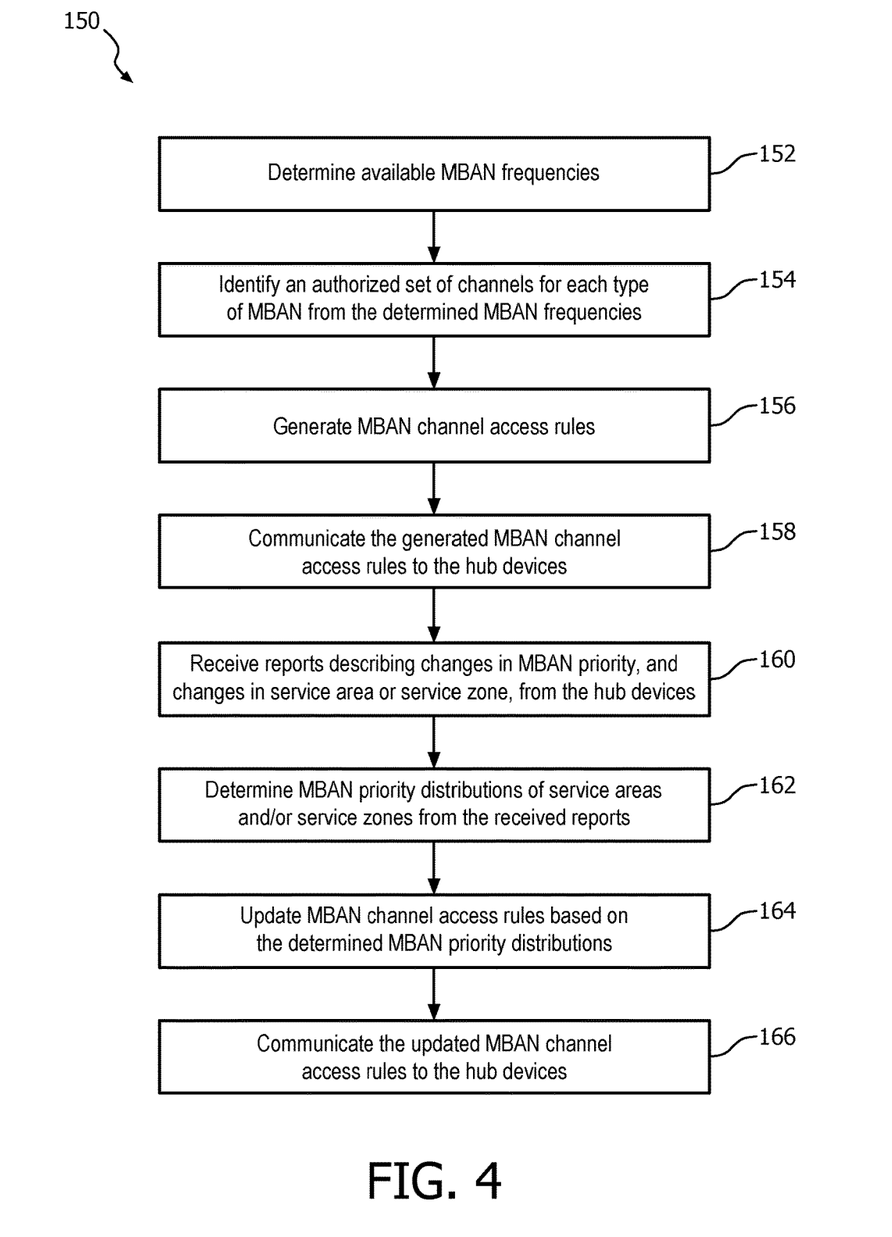
FIG. 4 illustrates an MBAN channel management scheme.

With reference to FIG. 4, a block diagram 150 illustrates operation of the MBAN channel management module 114. When initialized, the MBAN channel management module 114 determines 152 the available MBAN frequencies (e.g., based on control messages received from the MBAN coordinator 12, or from a configuration file), identifies 154 a set of MBAN channels for each type of MBAN (e.g., IEEE 802.15.6 or IEEE 802.15.4j) from the determined MBAN frequencies, generates 156 MBAN channel access rules for each service zone, or each service area of the access points 92, from the identified set(s) of MBAN channels, and communicates 158 the channel access rules to the hub devices 60 of the medical institution 50 over the backhaul communication network 88.

When an MBAN 62 of the medical institution 50 is powered on, the hub device 60 of the MBAN 62 connects to the access point with the service area within which the hub device 60 is located. When the hub device 60 establishes a connection to the backhaul communication network 88, the hub device 60 receives the MBAN channel access rules from the MBAN channel management module 114, typically by way of the serving access point of the hub device 60. Also, the hub device 60 receives an initial MBAN priority setting either from manual input or from the output of a CDS engine 94, 110, local or remote. Based on the received MBAN priority and the received channel access rules, the hub device 60 determines a set of MBAN channels on which it can operate and selects one from the set to start MBAN operations on. The hub device 60 reports its MBAN priority change to the MBAN channel management module 114 so the MBAN channel management module 114 can determine the MBAN priority distribution of each of the access points 92.

The CDS engine 94, 110 of the hub device 60, which can be implemented remote from the corresponding MBAN 62 or locally (e.g., at the hub device 60), continuously evaluates and/or predicts patient health status (i.e., patient acuity level), and updates the MBAN priority, based on patient real-time monitoring data (i.e., real-time physiological data collected by the corresponding MBAN 62). If there is an MBAN priority change due to patient health status change, the hub device 64 updates the set of MBAN channels that it can operate on. Also, the hub device 60 checks if its current operating channel falls in the new set. If not, the hub device 60 selects a new channel from the new channel set and switches the MBAN 62 to the new channel. Even more, the hub device 60 reports its MBAN priority change to the MBAN channel management module 114 through its serving access point.

When an MBAN 62 roams from one access point to another access point or from one service zone to another service zone, it receives the channel access rules for the new access point or new service zone during the handover process. Once the corresponding hub device 60 receives the channel access rules for the new access point or service zone, the hub device 60 updates the set of MBAN channels that it can operate on. Also, the hub device 60 checks if its current operating channel falls in the updated set. If not, the hub device 60 selects a new channel from the updated channel set and switches to the new channel. Even more, the hub device 60 reports the change of its serving access point to the MBAN channel management module so the MBAN priority distributions of both the old and new access points can be updated.

The MBAN channel management module 114 receives 160 reports describing changes in MBAN priority, and changes in service area or service zone, from the hub devices 60 of the medical institution 50. Based on these reports from the hub devices 60, the MBAN channel management module 114 determines 162 distributions of patient acuity levels for services areas and/or service zones. An MBAN priority distribution change of an access point or a service zone can trigger the MBAN channel management module 114 to dynamically update 164 the channel access rules for that access point or service zone. The updated channel access rules are communicated 166 to all the hub devices associated with the access point or service zone. Once a hub device 60 receives updated channel access rules, it updates the set of MBAN channels that it can operate on. Also, it checks if its current operating channel falls in the updated set. If not, it selects a new channel from the updated channel set and switches to the new channel.

The constituent actions (e.g., the determining 162) shown in FIG. 4 can also be units. A unit is software, hardware or a combination of the two. In that regard, it is to be appreciated that the MBAN channel management module 114 can be formed from a plurality of units, whereby the MBAN management module 114 can be software, hardware or a combination of the two.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a controller includes at least one memory and at least one processor, the processor executing processor executable instructions on the memory, or includes specialized hardware implementing a method; a user input device includes one or more of a mouse, a keyboard, a touch screen display, one or more buttons, one or more switches, one or more toggles, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A medical body area network (MBAN) channel management system comprising:
   at least one controller comprising an electronic processor executing stored instructions to:
      identify an available set of channels to be used by a plurality of MBAN systems;
      generate channel access rules describing a set of channels for each of a plurality of MBAN priorities, the channels of the set of channels being channels of the available set of channels, the plurality of MBAN priorities corresponding to MBAN priorities assigned to the plurality of MBAN systems, and the MBAN priorities assigned to the plurality of MBAN systems based on patient acuity level;
      communicate the channel access rules to the plurality of MBAN systems, wherein an MBAN system of the plurality of MBAN systems uses a channel from the set of channels corresponding to the MBAN priority assigned to the MBAN system;
      receive reports from the plurality of MBAN systems describing changes in MBAN priority and changes in service area or service zone; and
      update at least one of the channels from a first MBAN priority to a second MBAN priority based on a change in the patient acuity level by, during the updating, increasing the number of channels in the sets of channels for the most prominent MBAN priorities, the most prominent MBAN priorities being those MBAN priorities most prominent in MBAN priority distributions of the plurality of MBAN systems.

2. The MBAN channel management system according to claim 1, wherein the sets of channels for the plurality of MBAN priorities differ based upon the plurality of MBAN priorities.

3. The MBAN channel management system according to claim 1, wherein the at least one controller is further configured to:
generate the channel access rules for each of a plurality of service areas, or each of a plurality of service zones, of a medical institution within which the MBAN channel management system is used, the plurality of service areas corresponding to service areas of access points through which the plurality of MBAN systems communicate with the MBAN channel management system, and the plurality of service zones corresponding to collections of service areas;
wherein the MBAN system uses a channel from the set of channels corresponding to the priority of the MBAN system and the service area or service zone within which the MBAN system is located.

4. The MBAN channel management system according to claim 1, wherein each of the plurality of MBAN systems is located in one of a plurality of service areas, or one of a plurality of service zones, of a medical institution within which the MBAN channel management system is used, the plurality of service areas corresponding to service areas of access points through which the plurality of MBAN systems communicate with the MBAN channel management system, and the plurality of service zones corresponding to collections of service areas sharing common role.

5. The MBAN channel management system according to claim 1, wherein the set of channels for one of the plurality of MBAN priorities includes more channels than the sets of channels for lower MBAN priorities of the plurality of MBAN priorities.

6. The MBAN channel management system according to claim 1, wherein the set of channels for one of the plurality of MBAN priorities is a superset of the sets of channels for lower MBAN priorities of the plurality of MBAN priorities.

7. The MBAN channel management system according to claim 1, wherein one of the plurality of MBAN priorities assigned to a patient is greater than MBAN priorities of the plurality of MBAN priorities assigned to patients with lower acuity levels.

8. The MBAN channel management system according to claim 4, wherein the at least one controller is further programmed to:
determine MBAN priority distributions for the plurality of service areas, or the plurality of service zones, based on the received reports;
update the channel access rules based on the MBAN priority distributions; and
communicate the updated channel access rules to the plurality of MBAN systems.

9. A medical body area network (MBAN) channel management method comprising:
identifying an available set of channels to be used by a plurality of MBAN systems;
for each MBAN system of the plurality of MBAN systems, determining patient acuity of a patient monitored by the MBAN system;
generating channel access rules describing a set of channels for each of a plurality of MBAN priorities, the channels of the set of channels being channels of the available set of channels, the plurality of MBAN priorities corresponding to MBAN priorities assigned to the plurality of MBAN systems, and the MBAN priorities assigned to the plurality of MBAN systems based on the determined patient acuity level;
communicating the channel access rules to the plurality of MBAN systems, wherein an MBAN system of the plurality of MBAN systems uses a channel from the set of channels corresponding to the MBAN priority assigned to the MBAN system;
receiving reports from the plurality of MBAN system describing changes in MBAN priority and changes in service area or service zone; and
updating at least one of the channels from a first MBAN priority to a second MBAN priority based on a change in the patient acuity level by increasing the number of channels in the sets of channels for the most prominent MBAN priorities, the most prominent MBAN priorities being those MBAN priorities most prominent in the MBAN priority distributions.

10. The MBAN channel management method according to claim 9, wherein the sets of channels for the plurality of MBAN priorities differ based upon the plurality of MBAN priorities.

11. The MBAN channel management method according to claim 9, further including:
generating the channel access rules for each of a plurality of service areas, or each of a plurality of service zones, of a medical institution within which the MBAN channel management method is used, the plurality of service areas corresponding to service areas of access points through which the plurality of MBAN systems communicate with a device or system performing the MBAN channel management method, and the plurality of service zones corresponding to collections of service areas;
wherein the MBAN system uses a channel from the set of channels corresponding to the priority of the MBAN system and the service area or service zone within which the MBAN system is located.

12. The MBAN channel management method according to claim 9, wherein each of the plurality of MBAN systems is located in one of a plurality of service areas, or one of a plurality of service zones, of a medical institution within which the MBAN channel management method is used, the plurality of service areas corresponding to service areas of access points through which the plurality of MBAN systems communicate with a device or system performing the MBAN channel management method, and the plurality of service zones corresponding to collections of service areas sharing common role.

13. The MBAN channel management method according to claim 12, further including:
determining MBAN priority distributions for the plurality of service areas, or the plurality of service zones, based on the received reports;
updating the channel access rules based on the MBAN priority distributions; and
communicating the updated channel access rules to the plurality of MBAN systems.

14. The MBAN channel management method according to claim 9, wherein the set of channels for one of the plurality of MBAN priorities includes more channels than the sets of channels for lower MBAN priorities of the plurality of MBAN priorities.

15. The MBAN channel management method according to claim 9, wherein the set of channels for one of the plurality of MBAN priorities is a superset of the sets of channels for lower MBAN priorities of the plurality of MBAN priorities.

16. The MBAN channel management method according to claim 9, wherein one of the plurality of MBAN priorities assigned to a patient is greater than MBAN priorities of the plurality of MBAN priorities assigned to patients with lower acuity levels.

17. The MBAN channel management method according to claim 9, wherein the determining of patient acuity comprises receiving the patient acuity of the patient from a clinical decision support (CDS) engine comprising an electronic processor executing stored instructions.

18. A non-transitory computer readable medium carrying software which controls one or more processors to perform the method according to claim 9.

19. A hub device of a medical body area network (MBAN) system, the hub device comprising:
   at least one controller comprising an electronic processor executing stored instructions to:
   determine an MBAN priority based on a patient acuity level of a corresponding patient;
   receive MBAN channel access rules describing a set of channels for each of a plurality of MBAN priorities, the channels of the set of channels being channels of an available set of channels for a medical institution within which the hub device is used, the plurality of MBAN priorities including the MBAN priority and corresponding to MBAN priorities assigned to a plurality of MBAN systems of the medical institution;
   select a channel from the set of channels corresponding to the MBAN priority;
   configure an MBAN of the MBAN system to use the selected channel;
   receive reports from the plurality of MBAN system describing changes in MBAN priority and changes in service area or service zone; and
   update at least one of the channels from a first MBAN priority to a second MBAN priority based on a change in the patient acuity level by increasing the number of channels in the sets of channels for the most prominent MBAN priorities, the most prominent MBAN priorities being those MBAN priorities most prominent in the MBAN priority distributions.

\* \* \* \* \*